United States Patent [19]

Mantovani et al.

[11] Patent Number: 5,501,840
[45] Date of Patent: Mar. 26, 1996

[54] MULTILUMEN TUBING FOR CENTRIFUGAL BLOOD SEPARATOR

[75] Inventors: Marco Mantovani, Poggio Rusco; Stephano Sarti, Budrio; Ivo Panzani, Mirandola, all of Italy

[73] Assignee: Dideco S.r.l., Mirandola, Italy

[21] Appl. No.: 207,238

[22] Filed: Mar. 7, 1994

Related U.S. Application Data

[63] Continuation of Ser. No. 924,839, Aug. 4, 1992, abandoned.

[30] Foreign Application Priority Data

Aug. 5, 1991 [IT] Italy .................... MI91A2203

[51] Int. Cl.⁶ .................... B04B 5/04; A61M 1/34
[52] U.S. Cl. .................... 422/101; 422/100; 422/103; 138/111; 138/115; 138/118; 494/18; 494/20; 494/84
[58] Field of Search .................... 422/100, 101, 422/103, 58, 102; 138/111–113, 115–118.0, DIG. 11, DIG. 27; 494/17, 18, 20, 42, 84

[56] References Cited

U.S. PATENT DOCUMENTS

| | | | |
|---|---|---|---|
| 3,586,413 | 6/1971 | Adams | 359/503 |
| 4,108,353 | 8/1978 | Brown | 494/18 X |
| 4,109,852 | 8/1978 | Brown et al. | 494/18 X |
| 4,113,173 | 9/1978 | Lolachi | 494/18 X |
| 4,164,318 | 8/1979 | Boggs | 494/18 X |
| 4,194,684 | 3/1980 | Boggs | 494/18 X |
| 4,273,070 | 6/1981 | Hoefelmayr | 138/111 X |
| 4,296,882 | 10/1981 | Kobayashi | 494/18 X |
| 4,372,484 | 2/1983 | Larsson et al. | 494/14 |
| 4,389,206 | 6/1983 | Bacehowski et al. | 494/42 |
| 4,389,207 | 6/1983 | Bacehowski et al. | 494/42 |
| 4,459,169 | 7/1984 | Bacehowski et al. | 494/18 X |
| 4,531,932 | 7/1985 | Luppi et al. | 494/18 X |
| 4,741,593 | 5/1988 | Fochler | 138/111 X |
| 4,778,444 | 10/1988 | Westberg et al. | 494/56 |
| 4,834,890 | 5/1989 | Brown et al. | 210/739 |
| 4,865,081 | 9/1989 | Neumann et al. | 138/111 |
| 4,906,496 | 3/1990 | Hosono et al. | 428/36.9 |
| 4,936,820 | 6/1990 | Dennehey et al. | 494/1 |
| 4,950,401 | 8/1990 | Unger et al. | 210/360.1 |
| 4,963,420 | 10/1990 | Jarrin et al. | 428/36.9 |
| 4,975,055 | 12/1990 | LaPlante | 138/115 X |

FOREIGN PATENT DOCUMENTS

| | | |
|---|---|---|
| 0025660 | 5/1906 | Austria . |
| 0008776 | 8/1979 | European Pat. Off. . |
| 0241803 | 8/1986 | European Pat. Off. . |
| 0214803 | 3/1987 | European Pat. Off. . |
| 0363120 | 11/1990 | European Pat. Off. . |
| 0526869 | 8/1992 | European Pat. Off. . |
| 1172495 | 7/1962 | Germany . |
| 172495 | 6/1964 | Germany . |
| 1212370 | 3/1966 | Germany .................... 138/115 |
| 0000748 | of 1884 | United Kingdom . |

*Primary Examiner*—Jeffrey R. Snay
*Assistant Examiner*—Harold Y. Pyon
*Attorney, Agent, or Firm*—Popvich & Wiles

[57] ABSTRACT

The present invention relates to a multiple-duct tube for centrifugal separators for blood in particular, suitable for connecting a rotating connector to a stationary connector. The multiple-duct tube comprises, in a monolithic structure, a plurality of ducts which have parallel axes. The outer surface of the tube is defined by blended portions of walls of the peripheral ducts, so as to assume a lobate shape in a transverse cross-section.

7 Claims, 2 Drawing Sheets

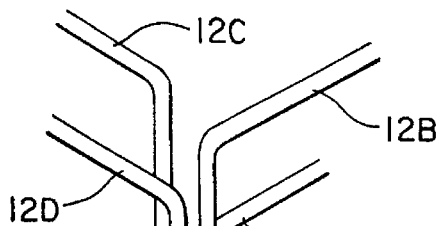
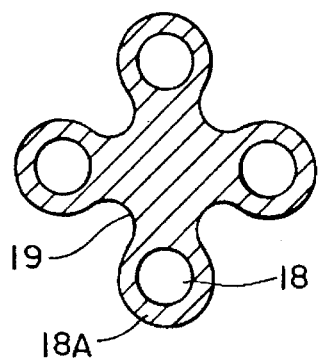
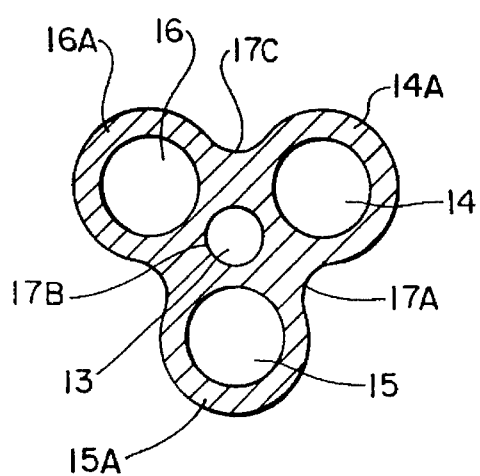
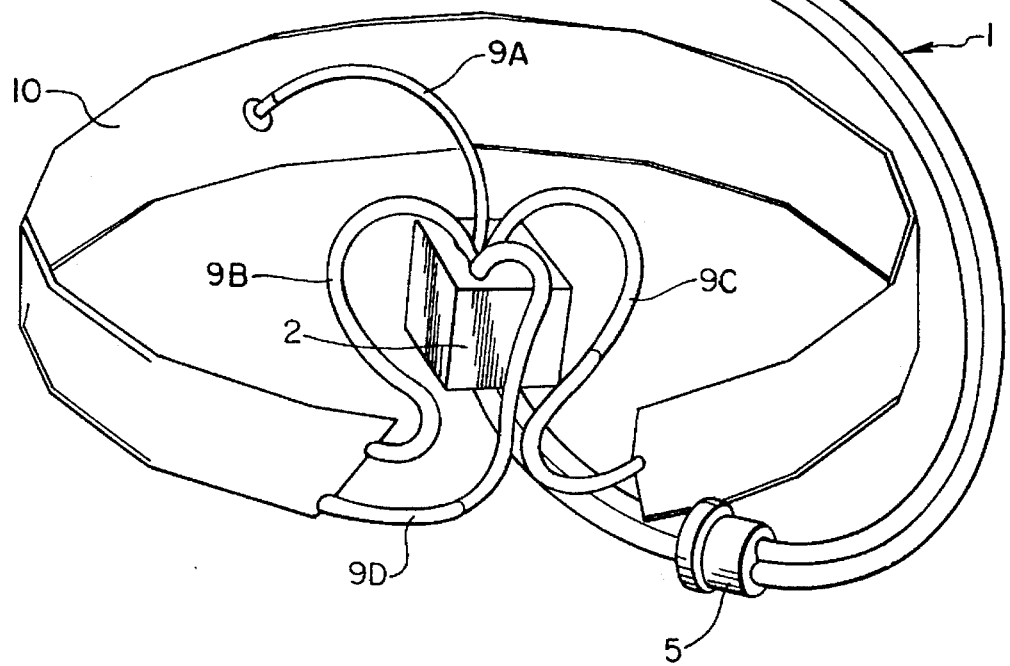

MULTILUMEN TUBING FOR CENTRIFUGAL BLOOD SEPARATOR

This is a continuation of application Ser. No. 07/924,839 filed Aug. 4, 1992, now abandoned.

BACKGROUND OF THE INVENTION

1. Field of the Invention

The present invention relates to a multiple-duct tube or tube assembly for centrifugal separators for blood in particular. The invention also relates to an apparatus embodying such tube and a method for making such tube.

2. Description of the Prior Art

It is known that many processes which aim to separate different components of a substance are performed by centrifuging the substance itself; this is the case, for example, of blood, which is centrifuged in order to separate various components, such as platelets, plasma and red cells, from whole blood.

Many types of centrifugal separators have been proposed, and one of these is disclosed in U.S. Pat. No. 3,586,413 granted to Adams.

In this type of separator, the multiple-duct tube, which is thus termed since it comprises a plurality of ducts in which the whole blood and the components separated therefrom by centrifugal action is conveyed, and are arranged so as to connect a connector associated with the rotating part of the machine, to a stationary connector, is rotated about the axis of rotation of the centrifugal separator at a rate equal to half the rotation rate of said separator. Branch lines extend from and are variously connected to the stationary connector for conveying blood or blood components to containers or to intracorporeal circulation.

This avoids the twisting of said tube despite the absence of rotating seals of the same on the terminal connectors. This fact is highly positive, since elimination of the rotating seals determines a saving in costs and eliminates the risk of contamination of the processed fluids.

The multiple-duct tube comprised in the described separator, also called "umbilical tube", is typically arranged in a curve which makes it resemble an inverted question mark. During operation, this tube is subjected to combined fatigue stress in which, besides flexure and tortion, the tensile stress due to the action of the centrifugal force is present. This stress can reach even very high values in view of the necessary high rotation rates.

The known art has proposed several different methods for manufacturing umbilical tubes capable of withstanding the stresses without undergoing mishaps.

U.S. Pat. No. 4,906,496 discloses two coaxial tubes with circular walls where the inner tube is kept separate by three dividing elements, so as to define four ducts, three peripheral ones and a central one.

U.S. Pat. No. 4,741,593 discloses three tubes kept parallel inside a sheath, providing a non-monolithic structure; a non-monolithic structure is also disclosed in U.S. Pat. No. 4,865,081.

There is also a type of umbilical tube in which four tubes, mutually joined at a generatrix, are jacketed proximate to their ends and are wrapped by a sheath at their intermediate portion.

In U.S. Pat. No. 4,108,353, U.S. Pat. No. 4,109,852 and U.S. Pat. No. 4,164,318 there is shown an umbilical tube comprising a plurality of ducts within a monolithic structure which has a perfectly circular perimeter in a transverse cross-section and is provided with tapered reinforcements at its ends.

The umbilical tube disclosed in U.S. Pat. No. 4,389,206, U.S. Pat. No. 4,389,207 and U.S. Pat. No. 4,459,169 comprises four plait-wound tubes rigidly associated by glueing.

However, all of the above umbilical tubes have drawbacks. In particular, all have a constructive complexity which arises from the need to give them the necessary stress resistance. This leads to an excessive cost for an element which, as is known, is intended to be used only once. Even despite the constructive complexity, the desired stress resistance is not always achieved in a fully satisfactory manner.

Attempts to reinforce umbilical tubes having a monolithic extruded structure by using glass or carbon fibers have also not yielded the expected results.

SUMMARY OF THE INVENTION

The aim of the present invention is therefore to provide a multiple-duct tube for centrifugal separators for blood in particular, which is capable of withstanding the stresses to which it is subjected during operation, while at the same time eliminating the structural complexity of prior structures. A further aim is to provide a multiple-duct tube which offers great reliability in operation and is capable of being manufactured at a very limited production cost. Still further aims include providing an improved blood separator embodying such a tube and a method of making the tube.

The proposed aims are achieved by a multiple-duct tube or tube assembly for centrifugal separators for blood in particular. According to the invention, the tube is adapted for connecting a rotating connector to a stationary connector, characterized in that the tube comprises, in a monolithic structure, a plurality of ducts which have parallel axes, and includes an outer surface defined by blended portions of walls of the peripheral ducts, so as to assume a lobate shape in a transverse cross-section.

Advantageously, the multiple-duct tube is characterized in that the monolithic structure is manufactured by extrusion with a material which withstands fatigue stresses, is blood-compatible and is adapted for allowing glueing the tube on contiguous elements made of PVC, constituted for example by a mixture of 30–40% PVC by weight and polyetheramide with alternating sequences.

Further characteristics and advantages will become apparent from the description of some preferred but not exclusive embodiments of the multiple-duct tube, according to the present invention, illustrated only by way of non-limitative example in the accompanying drawings.

DESCRIPTION OF THE DRAWINGS

FIG. 2 is a view of the umbilical tube according to the invention, comprised between the two terminal connectors connected to contiguous elements.

FIG. 3 is a transverse sectional view of the tube according to the invention, taken along the plane III—III of FIG. 2.

FIG. 4 is a transverse sectional view of an umbilical tube according to a further embodiment.

DESCRIPTION OF THE PREFERRED EMBODIMENT

Figure 1:
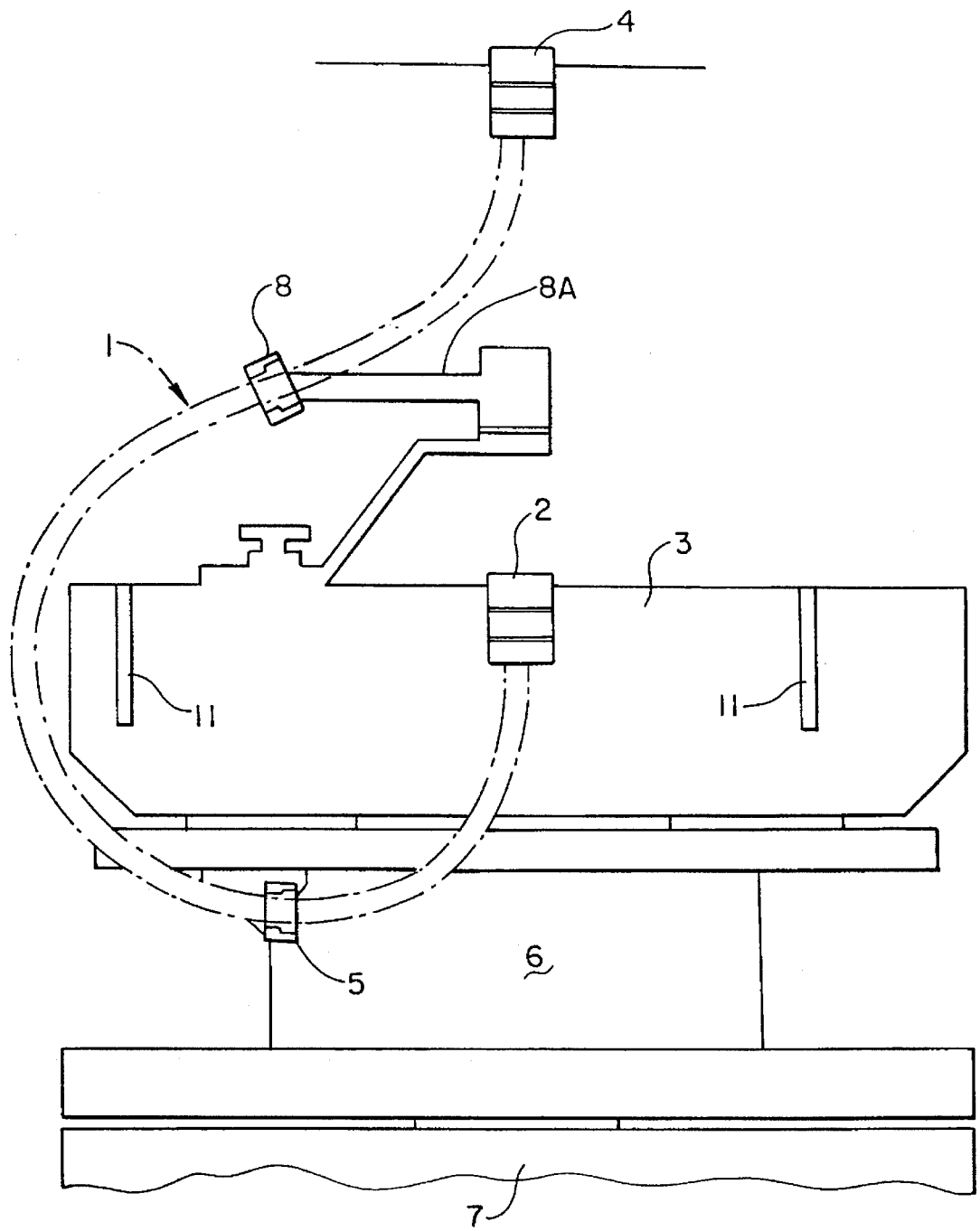
FIG. 1 is a schematic view of a centrifugal separator, merely by way of reference, in order to show the arrangement of an umbilical tube.

With reference to the above FIGS. 1, 2 and 3, the reference numeral 1 generally indicates the umbilical tube connecting the connector 2 to the stationary connector 4. The connector 2 is joined to the rotating plate 3 of the centrifugal machine, which rotates at a rate 2n, while the tube 1 is rotated at a rate n, equal to half the speed of the plate 3. The tube 1 is rotated by the bush 5 rigidly associated with the part 6 of the centrifugal machine, which is supported by the base 7 rotating exactly at said rate n.

This known situation allows, as mentioned, to eliminate rotating seals without thereby causing the umbilical tube 1 to twist, said tube being retained in position by the bush 8 which is supported by the arm 8a freely mounted on a rotation axis which coincides with the rotation axis of the machine.

To complete the description of known parts, it should be noted that the rotating connector 2 receives four lines 9a, 9b, 9c and 9d which are connected to the blood containment belt 10 intended to be inserted in the slot 11 of the rotating plate 3. It is also noted that the lines 12a, 12b, 12c and 12d branch from the stationary connector 4 for the conveyance respectively of platelets, whole blood, plasma and red cells to containers or to a patient.

The above description is of a centrifugal separator of the type to which the tube of the present invention has particular applicability. A further typical separator is disclosed in U.S. Pat. No. 3,586,413, which is incorporated herein by reference.

The multiple-duct tube 1 or tube assembly according to the invention comprises, in an extruded monolithic structure manufactured with a material described hereinafter, four ducts which have parallel axes and circular cross-sections. These ducts provide for the conveyance of the four above mentioned blood components. More precisely, the ducts of the embodiment of FIG. 3 include a central duct 13 and three peripheral ducts 14, 15 and 16. The ducts 14, 15 and 16 are defined in part by tube wall portions 14a, 15a and 16a, respectively which blend at 17a, 17b and 17c to form the trilobate shape of the perimeter of the outer surface of the tube 1.

In a particular embodiment, the cross-section of FIG. 3 has been given proportions such as to provide a diameter of the duct 13 equal to 1.5 mm and a diameter of the peripheral ducts 14, 15 and 16 equal to 2.5 mm with an outer tube wall thickness of about 1 min. Preferably the ducts 14, 15 and 16 are arranged with their centers evenly distributed on a circumference of a diameter equal to about 5.7 mm. Finally, the preferred embodiment shows the diameter of the generally circular arcs 17a, 17b and 17c to be equal to 3 mm, with the centers of said circular arcs being distributed on a circumference which has a diameter of about 8.5 mm.

The material extruded in order to obtain the monolithic structure of the tube 1 is advantageously constituted by a mixture of PVC of the type commercially known as API-FLEX T85 FC, which has a hardness of 85 Shore A, with polyether-amide with alternating sequences of the type commercially known as PEBAX 3533 SA 00, which has a hardness of 35 Shore D.

This material ensures good resistance to the combined fatigue stress which is typical of the umbilical tube during operation, is blood-compatible, and is furthermore suitable for allowing the glueing of the tube 1 to the contiguous lines made of PVC.

From what has been described, the extreme simplicity of the invention is evident; said invention is obtained by extrusion in its final shape, no further treatment being required, and the weight reduction which derives from the lobate shape of the cross-section leads to a reduction in the tensile stress produced by centrifugal action, allowing the multiple-duct tube according to the invention to operate without risk or mishaps.

Advantageously, the tube according to the invention comprises a central duct 13 or drain with an axis which substantially coincides with the axis of said tube, but a further embodiment of the type illustrated in FIG. 4 is also contemplated. According to this embodiment, the umbilical tube comprises four peripheral ducts such as 18 which define, with portions of their respective walls such as 18a, conveniently blended as in 19, a shape of the outer surface of the tube having the quadrilobate perimeter shown in the transverse cross-section of said FIG. 4.

The preferred embodiment of the invention described above is susceptible to numerous modifications and variations, all of which are intended to fall within the scope of the inventive concept. For example, the embodiments of FIGS. 3 and 4 show a multiple-duct tube with four ducts; however, it is contemplated that the advantages of the present invention can also be met with any number of ducts.

Further, each of the preferred embodiments of FIGS. 3 and 4 disclose a cross-section in which the lobate configuration shows a plurality of lobes which are generally equally or symmetrically spaced around the periphery of the tube. While this is the preferred structure, it is contemplated that the advantages of the present invention can be realized with a lobate structure in which the lobes are not equally spaced or are not necessarily of the same dimension. Still further, the preferred embodiments of FIGS. 3 and 4 show the individual lobes being blended together with an internal radius of curvature. It is contemplated, however, that adjacent lobes could be joined at a single point with no such radius of curvature.

Still further, in the description of the preferred embodiment, the present invention has been referred to as a multiple-duct tube having a plurality of ducts. It is contemplated that the invention can also be described as a tube assembly comprised of a plurality of elongated tube portions each having a duct defined by a tube wall. In such structure, each of the tube portions has a portion of its tube wall integrally joined to the tube wall of at least one adjacent tube portion, with the tube walls of a plurality of the tube portions defining the outer surface of the tube assembly to provide the generally lobate cross-sectional configuration.

Finally, in addition to the improved multiple-duct tube or tube assembly, the present invention also contemplates an improved blood separator embodying the above described multiple-duct tube as well as a method of making the tube. Such method includes preparing an extrusion head for forming a plurality of tube portions and extruding a selected material through such head to form the tube assembly in which each tube portion has a portion of its tube wall joined with the tube wall of at least one adjacent tube portion throughout its entire length. The method further includes extruding the material to form a tube assembly of indefinite length having a generally lobate cross-sectional configuration. The extruded tube assembly is then cut into desired lengths.

Although the description of the preferred and alternate embodiments has been quite specific, it is contemplated that various modifications could be made, including those described above, without deviating from the spirit of the present invention. Accordingly, it is contemplated that the scope of the present invention be dictated by the appended claims rather than by the description of the preferred embodiment.

We claim:

1. A centrifugal blood separator comprising:

a rotating plate having an axis of rotation about which the plate rotates;

a blood container removably coupled to the rotating plate;

a first connector connected to the rotating plate;

a plurality of lines connected between the blood container and the first connector for conveying blood components;

a second stationary connector spaced apart from the first connector along the axis of rotation of the rotating plate; and a tube connected between the first and second connectors, the tube being monolithic along its entire length between the first and second connectors and having a central axis and a plurality of lobes spaced peripherally about the central axis forming a multilobate outer wall in a transverse cross-section, each lobe having a duct for conveying a blood component, each duct having an axis parallel to the central axis.

2. The centrifugal blood separator of claim 1, wherein there are three lobes and three ducts.

3. The centrifugal blood separator of claim 1, wherein there are four lobes and four ducts.

4. The centrifugal blood separator of claim 1, further comprising a central duct coaxial with the central axis of the tube for conveying a blood component.

5. The centrifugal blood separator of claim 4, wherein the ducts have a circular cross-section.

6. The centrifugal blood separator of claim 1, wherein the tube is extruded from a material which is resistant to fatigue stress, is blood compatible, and can be glued to elements made of polyvinyl chloride.

7. The centrifugal blood separator of claim 6, wherein the material is a mixture of 30–40% polyvinyl chloride by weight and polyether-amide with alternating sequences.

* * * * *

UNITED STATES PATENT AND TRADEMARK OFFICE
CERTIFICATE OF CORRECTION

PATENT NO.  : 5,501,840
DATED       : March 26, 1996
INVENTOR(S) : Mantovani et al.

It is certified that error appears in the above-indentified patent and that said Letters Patent is hereby corrected as shown below:

Column 3, line 44, replace "min" with --mm--.

Signed and Sealed this

Nineteenth Day of August, 1997

Attest:

BRUCE LEHMAN

Attesting Officer

Commissioner of Patents and Trademarks